United States Patent [19]

Fruengel

[11] Patent Number: 4,839,529
[45] Date of Patent: Jun. 13, 1989

[54] ARRANGEMENT FOR IN SITU DETERMINATION OF QUANTITY OF TURBID MATTER AEROSOL AND/OR DUST IN FLUID WHICH FLOWS THROUGH A SPACE

[75] Inventor: Frank Fruengel, Hamburg-Schenefeld, Fed. Rep. of Germany

[73] Assignee: Impulsphysik GmbH, Hamburg-Schenefeld, Fed. Rep. of Germany

[21] Appl. No.: 86,688

[22] Filed: Aug. 18, 1987

[30] Foreign Application Priority Data

Aug. 20, 1986 [DE] Fed. Rep. of Germany ....... 3628072
Jul. 3, 1987 [EP] European Pat. Off. ........ 87109609.5

[51] Int. Cl.$^4$ ............................................. G01N 21/53
[52] U.S. Cl. ...................... 250/574; 356/339
[58] Field of Search ...................... 250/573, 574, 576; 356/338, 339

[56] References Cited

U.S. PATENT DOCUMENTS

| | | | |
|---|---|---|---|
| 3,700,333 | 10/1972 | Charlson et al. | 356/339 |
| 4,226,532 | 10/1980 | Berber et al. | 250/574 |
| 4,250,394 | 2/1981 | O'Connor | 250/574 |
| 4,273,443 | 6/1981 | Hogg | 250/574 |
| 4,343,552 | 8/1982 | Blades | 250/574 |
| 4,679,939 | 7/1987 | Curry et al. | 356/339 |

*Primary Examiner*—Edward P. Westin
*Attorney, Agent, or Firm*—Michael J. Striker

[57] ABSTRACT

An arrangement for in situ determination of the quantity of turbid matter, aerosol and/or dust in flue gas which flows through a flue by measurement of intensity of light irradiated by means of an optical transmitter in the flue, and dispersed on solid or fluid dispersion particles. The dispersion light is detected by a detector which is arranged outside of the bundle of rays of the transmitter and provided with a wide angle focusing optic. A woodsche horn absorbs the not dispersed part of the bundle of rays of the transmitter. The light source of the transmitter is formed as a xenon spark discharger with intensity maximum in the region of 350–600 nm, the detector signal is evaluated by an evaluating electronic circuit. The arrangement determines extremely low quantities of harmful matter.

50 Claims, 6 Drawing Sheets

ARRANGEMENT FOR IN SITU DETERMINATION OF QUANTITY OF TURBID MATTER AEROSOL AND/OR DUST IN FLUID WHICH FLOWS THROUGH A SPACE

BACKGROUND OF THE INVENTION

The present invention relates to an arrangement for in situ determination of the quantity of turbid matter, aerosol and/or dust in a fluid which flows through a space, by measurement of light which is scattered on solid or fluid particles of turbid matter, aerosols and/or dust of the fluid which is located in the space.

Emission tests are performed in many countries for determining the upper limits of harmful matter in exhaust gases. For performing the proper determinations and verifying the performance of the determinations, it is necessary to have available measuring devices which can measure very small quantities of for example dust in an exhaust flue (chimney) with a concentration under 100 microgram per cubic meter.

The known arrangements for conventional measuring processes make conclusions from a transmission reduction about the content of harmful matter. However, they do not produce useful results with a transmission reduction of under 0.1 promill.

Other processes operate in accordance with the in vitro principle. In accordance with this principle a probe is taken from the exhaust flue by a suction mechanism and it is supplied for evaluation to a measuring cell. In this process inhomogeneties in the stream cannot be taken into consideration.

In accordance with further processes a probe is taken from the measuring space and analyzed in a laboratory.

SUMMARY OF THE INVENTION

Accordingly, it is an object of the present invention to provide an arrangement for in situ determination of the quantity of turbid matter, aerosol and/or dust in a fluid which flows through a space, with which also a small quantity of harmful matter is determined directly (in situ) and exactly in flowing fluid. Thereby a reliable monitoring of the quantity of harmful matter is possible over long periods of months. In particular, the quantity of turbid matter, aerosol and/or dust of particles in submicrometer region for example in flue gases can be determined. The quantity in the size order of several 10⋅ microgram per cubic meter can be determined also in small spaces with dimensions of the cross-section in the region of for example 40 cm.

In keeping with these objects and with others which will become apparent hereinafter, one feature of the present invention resides, briefly stated, in an arrangement for in situ determination of the quantity of turbid matter, aerosol and/or dust in a fluid which flows through a space by measurement of light scattered on solid or fluid particles of turbid matter, aerosols and/or dust of a fluid located in a space, wherein the arrangement has a light emitting optical transmitter with a light source, and a detector with wideangled receiving characteristic arranged so that it receives only scattering light scattered on the particles from the light emitted by the optical transmitter.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
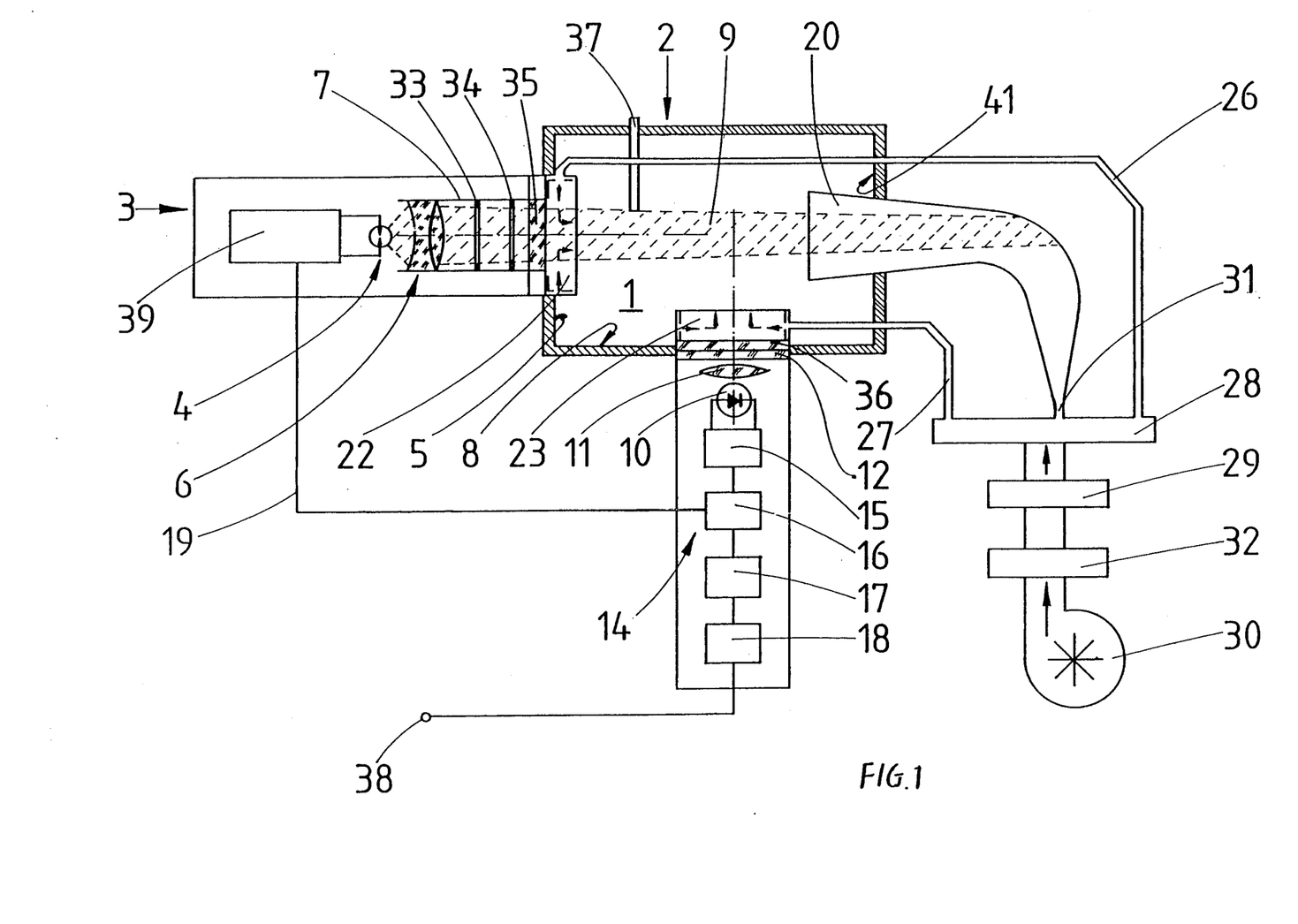
FIG. 1 is a view schematically showing an arrangement for measuring the quantity of dust with a Woodsche horn as an absorber, in accordance with the present invention.

An arrangement shown in FIG. 1 is arranged on a flue (chimney) for measuring the quantity of turbid matter, aerosols and/or dust in a flue gas which flows through a drafting space 1 of the flue 2. It has an optical transmitter 3 with a light source 4 and an optical system 6, a photodiode 10 as a detector with a connected wide angle focusing optic 11, an optical filter 12 and an evaluating electronic circuit 14, as well as a Woodsche horn 20 as an absorber.

The light source 4 is formed as a xenon spark discharger 4 which radiates in a half space and is located in a passage 7 which opens into the flue space 1 via an opening in the left flue wall 5. The wall of the passage 7 is light absorbing. The xenon spark discharger is located in a focus of the optical system 6 formed by anastigmats. Two diaphragms 33 and 34 are arranged in the passage 7 between the anastigmats 6 and the outlet of the passage. The wide angle focusing optic 11 is arranged in an opening of the lower flue wall 8. The optical filter 12 and the photodiode 10 located in the focus of the optic 11 are arranged after the wide angle focusing optic 11. The wide focusing optic 11 is an anastigmat or a coma-and opening error-free astigmat with an angular field of view of about 40°–80°. It can also be formed as a condenser lens. The optical axes of the anastigmats 6 and the wide angle optic 11 extend perpendicularly to one another. The Woodsche horn 20 extends into the flue space 11 through an opening which is provided in a flue wall 41 opposite to the xenon spark discharger 4 and which is coaxial with the optical axis of the anastigmats 6.

The anastigmats 6 and the wide angle optic or objective 11 are covered from the flue space 1 by a respective protective glass 35 and 36. An annular nozzle 22 and 23 sits on the protective glasses 35 and 36 coaxially to the optical axis of the anastigmats 6 or the wide angle objective 11. The diameter of the annular nozzles 22 and 23 is greater than the diameter of the opening of the anastigmats 6 or the wide angle objective 11. The annular nozzles 22 and 23 are each connected with an air distributor 28 via a pipe conduit 26 and 27. The air distributor 28 is connected with a blower 30 via a fine filter 29 and an air prefilter 32. The air which flows from the annular nozzles 22 and 23 radially to the optical axis of the anastigmats 6 or wide angle objective 11 prevents depositing of turbid matter, aerosol and/or dust on the protective glasses 35 and 36. A further pipe conduit 31 leads from the air distributor 28 through the small end of the Woodsche horn 20. The Woodsche horn 20 is blown laminarly from its small end with cleaned air, so that in its expanded end located in the flue space 1 no turbid matter, aerosol and/or dust can penetrate and any deposit in the Woodsche horn is prevented.

The photodiode is connected electrically with the evaluating electronic circuit 14 which includes a filter amplifier 15, a gate circuit 16, a measuring value preparation 17 and a driver stage 18. The evaluated measuring values are supplied via the driver stage 18 and a terminal 28 to a peripheral indicating device.

The xenon spark discharger 4 is supplied from a pulse generator 39 and sense polychromatic light pulses with a period of 0.5 to 5 microseconds, for example, of 2 microseconds, with a pulse energy of 0.05 to 0.5 J, for example 0.1 J in spectral region of 350–600 nm. The sent out light is bundled by anastigmats 6 in a parallel or slightly converging bundle of rays 9. The bundle of rays 9 is such that after passage through the space 1 it is completely absorbed by the Woodsche horn 20.

The inventive arrangement determines the quantity of turbid matter, aerosol and/or dust in a flue gas which flows through the drafting space 1 of the flue 2 by means of a light scattering measurement. Dielectric and metallic dust particles and liquid drops scatter the light sent by the transmitter 3, and the angle of scattering of the scattered light mainly depends from the wave length of the radiated light, the diameter and the dielectric constant of the solid or fluid particles. The intensity of the scattering light scattered over a predetermined angle depends, with identical particles and predetermined light wave lengths, only from the number of the particles, or in other words from the quantity of turbid matter, aerosol, and/or dust. It has been shown that in flue gases solid and fluid particles appear with diameters in sub-micrometer region, which produce an especially high scattering light intensity during irradiation with the polychromatic light of the xenon spark discharger 4 which emits mainly in wavelength region of approximately 350–600 nm. Particles of different diameter scatter the light of the xenon spark discharger 4 in the angular region detected by the wide angle focusing optic 11. What is important for detecting the scattering light of particles of different diameters is, on the one hand, the wide angle characteristic of the optic 11 and, on the other hand, the spectral band width of polychromatic light sent from the spark discharger 4 of approximately 250 nm, with which the angle dependency of the scattered light relative to monochromatic light is reduced. The number of particles can be determined therefore from the intensity of the scattering light detected by the detector 10. With known composition of the dispersion particles, the quantity of particles in weight per volume can be determined, based on the intensity of the detected scattering light. The calibration of the arrangement is performed by fluids with known different quantities of particles, and the evaluation electronic circuit evaluates the detector signal for each quantity of particles.

The xenon spark discharger 4 has electrodes of a tungsten sintered metal with addition of nickel, barium and/or aluminum. For preventing evaporation of electrode material from the electrodes which can deposit on piston, the xenon spark discharger 4 operates with a fraction of its nominal power, for example only approximately 10% of the nominal power. The energy per electrical pulse is so small that the electrode material in electrical pulse operation remains in the region of elastic deformation and thereby does not produce any material losses. The reduction of the electrical pulse energy means, however, also a reduction of the emitted energy of the light pulse which is compensated by the utilization of the anastigmats 6 with high opening ratio. Instead of the anastigmats 6, can also be a coma- an opening error-free astigmat can be used.

Since quantum efficiency of the photodiode 10 is temperature dependent, the photodiode 10 is held by a not shown heating device at the highest expected ambient temperature of 50° C. Similarly, the whole electronic circuit is thermally stabilized by means of the heating arrangement to 50° C.

The Woodsche horn 20 absorb the bundle of rays 9 completely and thereby prevents that light from the flue wall 41 be reflected in the detector 10. The anastigmat 6 produces scattering light by minimum in homogenities in its glass body and on its outer surface. Since the light source 4 with the anastigmats 6 in the channel 6 with light absorbing walls is arranged at a distance from the space 1, this scattering light is prevented from reaching the detector 10. The radial diaphragms 33 and 34 are used for the same purpose.

The optical filter 12 is permeable in the region of 350–500 nm and prevents focusing of the falling light (artificial or daylight) which takes place in the space 1 from focusing from the wide angle focusing optic 11 onto the detector 10.

The further improvement of the signal-noise ratio is achieved by the electrical filter amplifier 15 and the gate circuit 16 which is controlled via a trigger conductor 19 from a pulse generator 39 synchronously with the sent out light pulses. Thereby the received scattering light is evaluated only during the period of each light pulse.

The light flow process of the light pulses is stable in time and the light pulses have a length of 0.5–5 microseconds, for example, 1 microsecond with a rise time up to impulse peak of 0.25 microseconds. The time process of the scattering pulse corresponds to that of the light pulse sent from the xenon spark discharger 4. For allowing a passage of only the scattering light pulses, the filter amplifier 15 has a frequency band of 50–1,000 kHz, which substantially corresponds to the Fourier spectrum of the light pulse without direct current portion.

The measuring value preparation 17 is connected with the output of the gate circuit 16 and has a peak value detector which determines the peak values of the detector signals, a storage in which respectively a sequence of peak values is stored, and an average value generator which calculates the average value from the stored peak value sequence and stores the same in the storage. The respective average value and in some cases additionally the peak value sequence are sent via the driver stage 18 and the terminal 38 to one or more peripheral not shown recording and/or indicating devices.

For providing especially high sensitivity, it is recommended to use the spark discharger of the light source 4 with a xenon filling with a filling pressure which is over 1 bar. The electrode material must be extremely dust-free. For example, an electrode alloy can be used which is sintered together from sintered tungsten and/or nickel. It is thereby achieved that the electrodes have a service life of several billions light pulses.

The evaluating electronic circuit 14 is designed so that a feed current of at least 4 mA flows at its output 38. When the feed current exceeds this limit, it is connected with a switching defect or a failure of the supply voltage and indicated by a not shown alarm generator.

For operation monitoring, a light dispersion pin 37 is introduced into the space 1 so that it extends into the bundle of rays 9. The produced additional scattering light results in a noticeable increase of the detector signal which is evaluated by the evaluating electronic circuit 14 and indicates the operational readiness of the arrangement.

Figure 2:
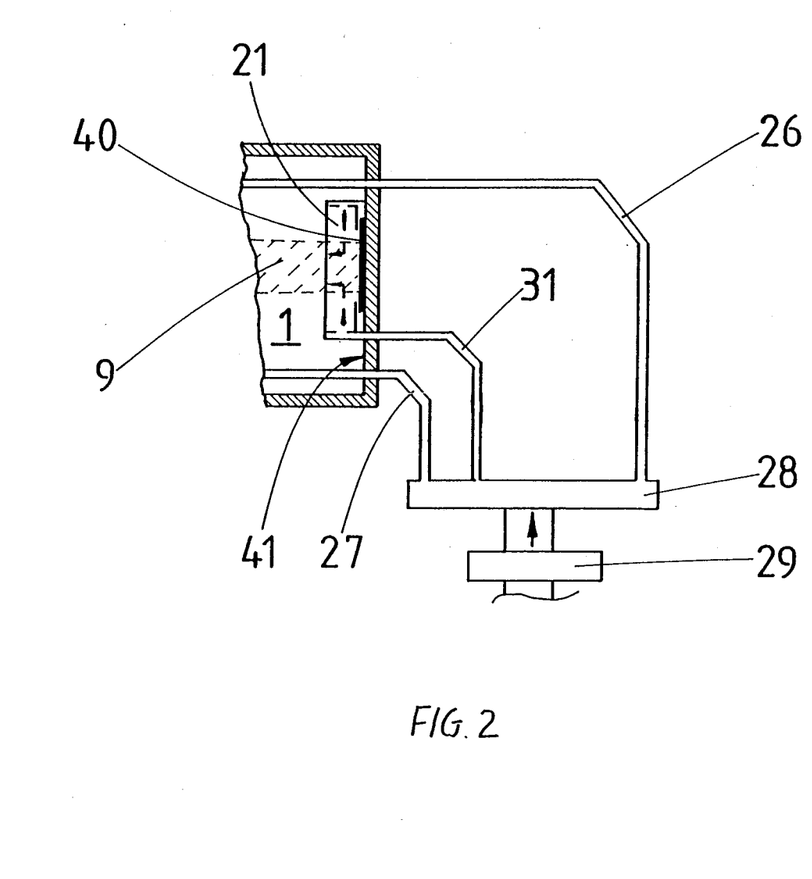
FIG. 2 is a partial view of a laminar absorber in accordance with a first embodiment of the invention.
Figure 3:
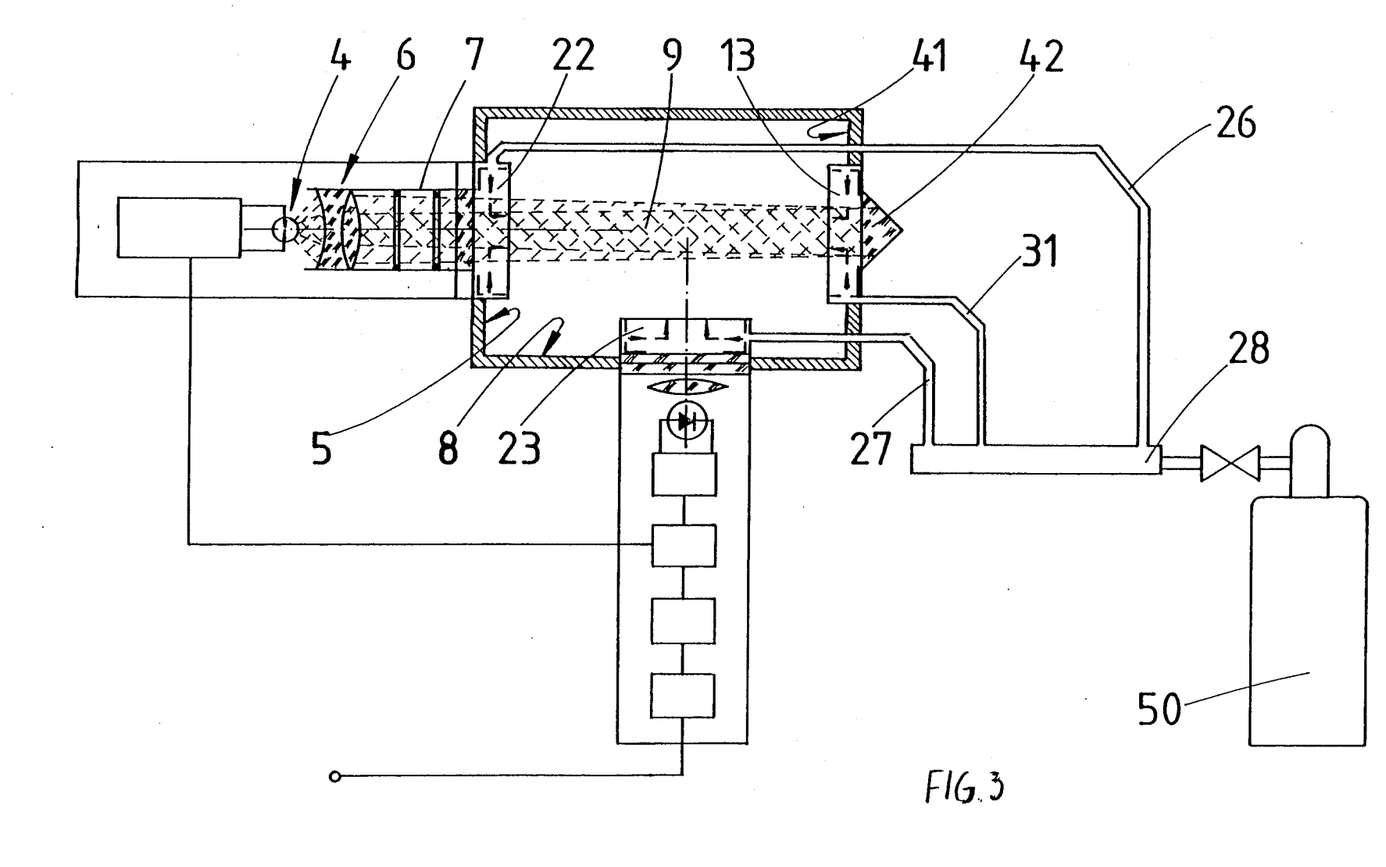
FIG. 3 is a view schematically showing a second embodiment of the arrangement of the present invention with a reflector.

The embodiment of the arrangement shown in FIG. 2 differs from the embodiment of FIG. 1 in that instead of the Woodsche horn 20, a laminar absorber 40 is arranged at the inner side of the flue wall 41. The outer surface of the absorber 40 is protected by clean air which flows from the annular nozzle 21 from contamination by turbid matter, aerosol, and/or dust. The embodiment of the arrangement shown in FIG. 3 differs from the embodiment of FIG. 1 in that, instead of the Woodsche absorber 40, a mirror 42, for example, a triple reflector, is arranged opposite to the light source 4. It deflects the light beam 9 back to the passage 7. The same ray bundle 9 passes therefore twice in the space 1, so that the scattering signal is approximately doubled. The mirror 42 is protected from contamination by air which flows from an annular nozzle 13, supplied to the annular nozzle 13 from a pressure air container 50. The utilization of air from the pressure air container 50 is always of advantage when the arrangement deals with short measuring time of only several hours and network terminals of high power for the blower such as for example in an airplane are difficult to install.

Figure 4:
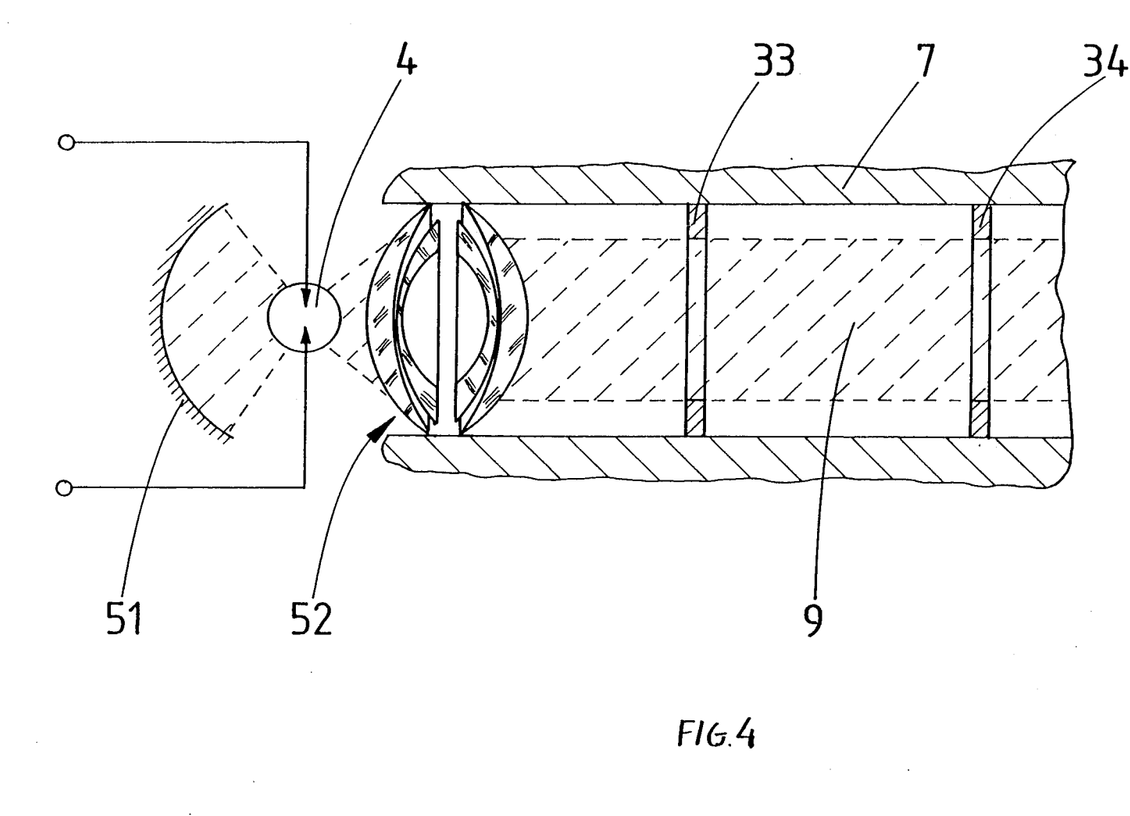
FIG. 4 is a partial view of an optical transmitter with a hollow mirror and lens system of a third embodiment of the arrangement in accordance with the present invention.

In the embodiment of the arrangement shown in FIG. 4 the spark discharger 4 irradiates in approximately full spatial angle. A hollow mirror 51 is arranged near the spark discharger 4 at its side opposite to the space 1 and has a focal length which corresponds to that of optical system 6. The hollow mirror 51 focuses the light of the spark discharger 4 falling on it near its light arc. This doubles the light yield in the bundle of rays 9.

Figure 5:
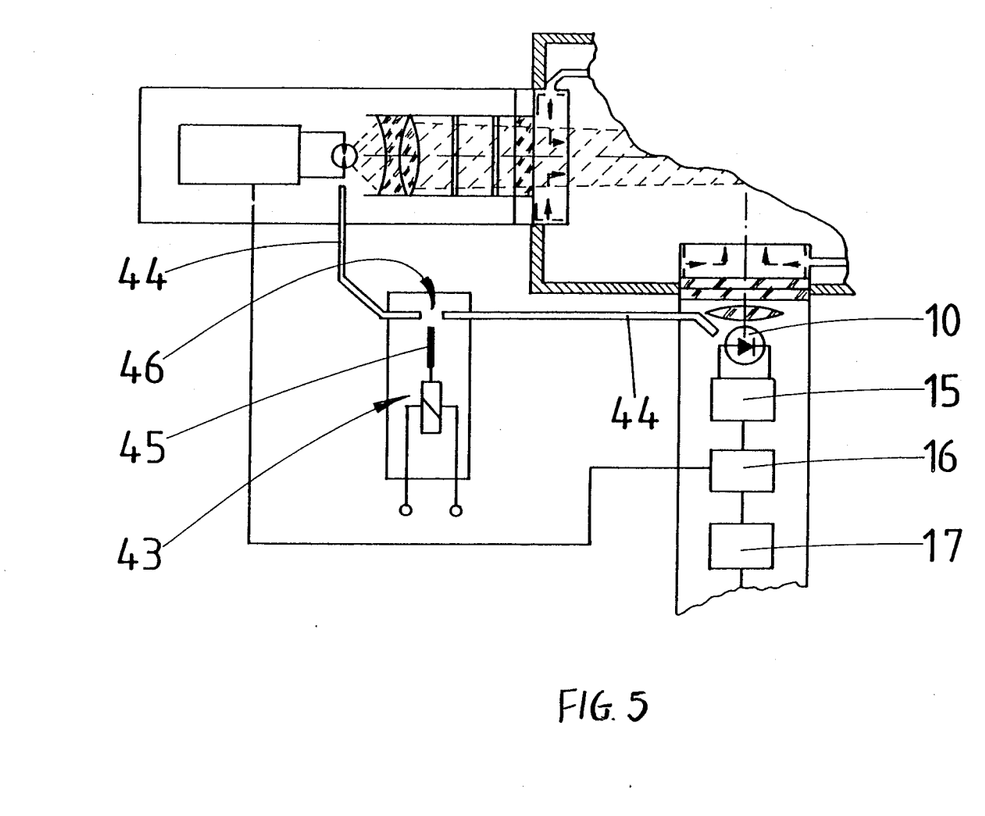
FIG. 5 is a schematic view of the arrangement in accordance with a fourth embodiment of the invention with a subdivided light conductor for operation monitoring.

A further embodiment of the arrangement of FIG. 1 is shown in FIG. 5. It provides for a further possibility of operation examination with a light conductor 44 which leads from the spark discharger 4 to the detector 10. The light conductor 44 has a separation point 46 in which an optic light filter 45 is arranged. The filter 45 is composed of several, for example three grey stages and a light-impermeable part and for operation examination is displaceable by means of an electromechanic displacing device 43. In operation the light-impermeable part is located in the separation point 46. For operation examination, the filter 45 is displaced by means of the displacing device 43 so that light is supplied from the spark discharger 4 through the light conductor 44 to the detector 10 and is weakened in correspondence with the grey stage. The device is operational when the evaluating electronic circuit 14 supplies with the selected grey stage a predetermined signal.

Figure 6:
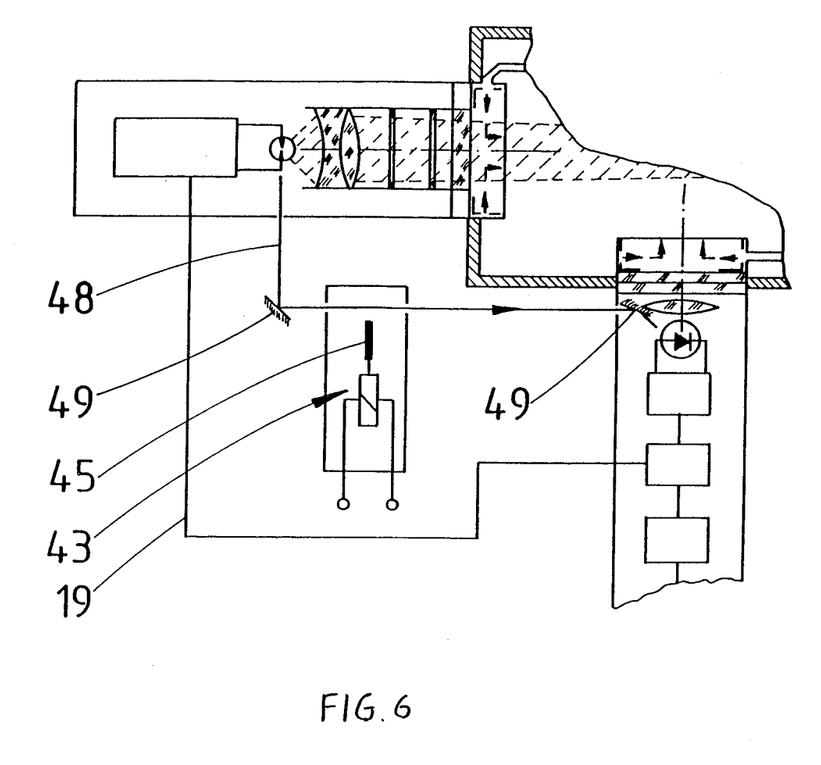
FIG. 6 is a schematic view of a fifth embodiment of the arrangement in accordance with the present invention with a light transmitting track for operation monitoring of the arrangement in accordance with the present invention.

Another embodiment of the arrangement of FIG. 5 is shown in FIG. 6. Here, instead of the separated light conductor 44, a light transmitting track 48 with a deviating mirror 49 is provided.

Instead of the gas discharge lamp 4 with xenon filling, also other gas fillings can be used. Care should be taken only that the light emitted by the gas discharge lamp 4 be polychromatic and its average wavelength correspond approximately to the diameter of the solid or fluid dispersion particles.

Instead of the photodiode 10, also a high vacuum photocell can be used as a detector.

For flues 2 with great diameters, the provision of openings in the flue walls for the transmitter 3, the detector 10 with wide angle focusing optic 11 and the absorber 40 can be dispensed with. The above mentioned part of the arrangement can be mounted on a frame which is arranged on the inner wall of the flue 2 or suspended in the flue 2.

In a not shown embodiment of the arrangement of FIG. 1 a photodiode 10 can be provided with greater aperture angle (angular displacement). Since the photodiode 10 has itself wide angle characteristic, the focusing optic 11 can be dispensed with, while of course the measurement sensitivity of the arrangement is reduced.

The inventive arrangement can be used generally where the measurement of a very small quantity of harmful matter must be performed. The fields of application include especially flues in the lead, asbestos, or zinc industry. Measurements are also possible on airplanes or measurements in measuring towers in free atmosphere, in which, for example, the concentration of a fume bell contains dust, within approximately 20 km visual range, about 20 micrograms per cubic meter.

It will be understood that each of the elements described above, or two or more together, may also find a useful application in other types of constructions differing from the types described above.

While the invention has been illustrated and described as embodied in an arrangement for in situ determination of the quantity of turbid matter, aerosol and/or dust in a fluid which flows through a space, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An arrangement for in situ determination of the quantity of aerosol in a flue gas which freely flows through a space in situ by measurement of light scattered on particles of aerosol which freely flows in the space, characterized by an optical transmitter with a light source which emits a light into the space in situ toward the freely flowing aerosol; and a detector which is arranged so that from the light emitted by the optical transmitter it receives only light which is scattered on the particles of the aerosol which freely flows in the space in situ.

2. An arrangement as defined in claim 1, characterized in that the wide angle receiving characteristic of the detector is produced by a pre-connected wide angle focusing optic which has such angular field of view that light which is scattered forwardly, rearwardly and around 90° is focused on the detector.

3. An arrangement as defined in claim 2, characterized in that the wide angle focusing optic is an anastigmat.

4. An arrangement as defined in claim 2, characterized in that the wide angle focusing optic is a coma-and opening failure-free anastigmat.

5. An arrangement as defined in claim 2, characterized in that the wide angle focusing optic is a condenser lens, while the detector is a photodiode.

6. An arrangement as defined in claim 1, characterized in that the optical transmitter has an optical system which has an opening ratio of approximately 1 and which bundles the light emitted from the light source to a bundle of rays.

7. An arrangement as defined in claim 6, characterized in that the optical system is an anastigmat.

8. An arrangement as defined in claim 6, characterized in that the optical system is a coma- and opening error-free anastigmat.

9. An arrangement as defined in claim 6, characterized in that the optical system is composed of a hollow mirror and a lens system with at least approximately equal focal length, the light source being formed by a gas discharge flash bulb with a light arc and arranged between the hollow mirror and the lens system, the hollow mirror being arranged to focus light of the gas discharge flash bulb falling on it near the light arc, and the bundle of rays exiting from the lens system.

10. An arrangement as defined in claim 1, characterized in an absorber arranged relative to the optical transmitter at its side which is opposite to the space and absorbing the light which is emitted by the optical transmitter and not scattered.

11. An arrangement as defined in claim 10, characterized in that the absorber is formed as a Woodsche horn.

12. An arrangement as defined in claim 10, characterized in that the optical system is formed so that the light emitted from the optical transmitter and not dispersed is focused at the absorber.

13. An arrangement as defined in claim 1, characterized in a reflector which is arranged relative to the optical transmitter at its side opposite to the space and reflects back the light emitted by the optical transmitter in direction to the transmitter, so that the reflected light is again scattered on the particles.

14. An arrangement as defined in claim 13, characterized in that the reflector is formed as a triple mirror.

15. An arrangement as defined in claim 1, characterized in that the space through which the fluid flows is a drafting space of a flue.

16. An arrangement as defined in claim 6, characterized in that the light source and the optical system are arranged in a passage which opens into the space and which has a light-absorbing wall and has a distance from an optical axis of the wide angle focusing optic which is such that the light of the light source scattered in the optical system cannot reach the detector.

17. An arrangement as defined in claim 16, characterized in an aperture which radially limits the bundle of rays in the passage.

18. An arrangement as defined in claim 13, characterized in that the optical transmitter has an optical system, and the optical system and the reflector are formed and arranged so that the reflected light is supplied into the passage.

19. An arrangement as defined in claim 1, characterized in that the light source is a gas discharge flashing bulb.

20. An arrangement as defined in claim 19, characterized in that the gas discharge flashing bulb is arranged so that it operates with only a fraction of its nominal power for insuring a long time stability of its irradiation.

21. An arrangement as defined in claim 19, characterized in that the gas discharge flashing bulb has a xenon filling and electrodes composed of a tungsten sintered metal with an additive selected from the group consisting of nickel, barium, aluminum and a combination thereof.

22. An arrangement as defined in claim 1, characterized in a light outlet surface for exiting the light of transmitter and to the space, a scattering light inlet surface for introducing the scattering light from the space to to the detector, and at least one blower with a fine dust filter which ventilates the light outlet surface and the scattering light inlet surface with clean air so as to prevent deposits of turbid matter, aerosol and/or dust.

23. An arrangement as defined in claim 1, characterized in a light outlet surface for exiting the light of the transmitter into the space, a scattering light in the surface for introducing the scattering light from the space to the detector, and a pressure gas container which blows pressure gas to the light outlet surface and the scattering light inlet surface for preventing deposits of turbid matter, aerosol and/or dust.

24. An arrangement as defined in claim 1, characterized in a light outlet surface for exiting the light of the transmitter into the space, a scattering light inlet surface for introducing the scattering light from the space to the detector, and an annular nozzle which blows the light outlet surface and the scattering light inlet surface for preventing deposits of turbid matter, aerosol and/or dust.

25. An arrangement as defined in claim 11, characterized in means for laminarly blowing the Woodsche horn from its smaller side with a purified air to prevent entering of turbid matter, aerosol and/or dust through its expanded end and depositing the same on its walls.

26. An arrangement as defined in claim 1, characterized in a light scattering element arranged in the light of the transmitter for producing additional scattering light increasing a detector signal which is evaluated and indicates operational readiness of the arrangement.

27. An arrangement as defined in claim 1, characterized in that the optical transmitter sends light pulses and the detector has an evaluating electronic circuit for receiving scattering signals which operate synchronously with the sent light pulses so as to evaluate the received scattering light only during the time of each light pulse.

28. An arrangement as defined in claim 27, characterized in that the optical transmitter sends the light pulses with predetermined time intensity course, and the evaluating electronic circuit is a filter amplifier with a frequency substantially corresponding to the Fourier spectrum of the light pulse without direct current component.

29. An arrangement as defined in claim 1, characterized in that the optical transmitter sends light pulses with a duration of 0.5–5 microseconds.

30. An arrangement as defined in claim 28, characterized in that the filter amplifier has a band width of substantially 50–1000 kHz.

31. An arrangement as defined in claim 1, characterized in that the optical transmitter has a wide band emission spectrum in the region of substantially 350–500 nm and the detector for improving the signal-noise ratio of the received scattered light is preceded by a wide band optical filter which allows passage of the emission spectrum in the region of substantially 350–600 nm.

32. An arrangement as defined in claim 1, characterized in a light conductor which leads from the optical transmitter to the detector and conducts a part of light from the transmitter to the detector, and an element cooperating with the light conductor to receive the conducted light part so as to determine the operability of the arrangement.

33. An arrangement as defined in claim 32, characterized in that the element is arranged in a light path of the light conductor.

34. An arrangement as defined in claim 32, characterized in that the element is arranged between the light conductor and the optical transmitter.

35. An arrangement as defined in claim 32, characterized in that the element is arranged between light conductor and the detector.

36. An arrangement as defined in claim 32, characterized in that said element is formed as a blocking element.

37. An arrangement as defined in claim 32, characterized in that the element is formed as a damping element.

38. An arrangement as defined in claim 32, characterized in that the light conductor is formed as a glass fiber line.

39. An arrangement as defined in claim 32, characterized in that the light conductor has a core of a synthetic plastic material.

40. An arrangement as defined in claim 1, characterized in a light transmitting track provided with a deviating mirror and leading from the optical transmitter to the detector to conduct a part of light from the transmitter to the detector, and an element arranged in the light transmitting track to receive the conducted light part so as to determine the operability of the arrangement.

41. An arrangement as defined in claim 32, characterized in means for electromagnetically activating the element for determining the operability of the arrangement.

42. An arrangement as defined in claim 27, characterized in that the evaluating electronic circuit which evaluates the scattering signal received by the detector releases an alarm in the event of exceeding a predetermined current level of an output signal for indicating error measurements or switching defects.

43. An arrangement as defined in claim 1, characterized in that the optical transmitter sends light pulses and an evaluating electronic circuit with a storage is provided for scattering light signals of the detector so that it stores and evaluates specific values of the detected scattering light signals.

44. An arrangement as defined in claim 43, characterized in that said evaluating electronic circuit is formed so that it stores and evaluates peak signals of the detected dispersion light signals.

45. An arrangement as defined in claim 43, characterized in that the evaluating electronic circuit stores and evaluates average values of the detected dispersion light signals.

46. An arrangement as defined in claim 27, characterized in means for temperature stabilizing the detector and parts of the evaluating electronic circuit.

47. An arrangement as defined in claim 1, characterized in that the detector is a photodiode.

48. An arrangement as defined in claim 1, characterized in that the detector is a high vacuum photocell.

49. An arrangement as defined in claim 1, characterized in that the optical transmitter is a transmitter which sends polychromatic light.

50. An arrangement for in situ determination of the quantity of aerosol in a flue gas which freely flows through a space in situ by measurement of light scattered on particles of aerosol which freely flows in the space, characterized in an optical transmitter with a gas discharge flashing bulb supplied from a power generator, to produce light pulses with a duration of 0.5–5 microseconds with a pulse energy of 0.05–0.5 J in spectrum approximately 350–600 nm, and an anastigmat which bundles the light of the gas discharge flashing bulb to a bundle of rays which is supplied into the space in situ toward the freely flowing aerosol, a detector with focusing optic and an evaluating electronic which is arranged outside the bundle of rays so that it receives from the bundle of rays sent by the optical transmitter only scattering light scattered on the particles of the aerosol which freely flows in the space in situ, the evaluating electronic has 50–1000 kHz and a gate circuit which allows passage of the output signal of the detector from the pulse generator synchronously only during the duration of the light pulse.

* * * * *